(12) United States Patent
Datta et al.

(10) Patent No.: US 8,211,692 B2
(45) Date of Patent: *Jul. 3, 2012

(54) BIOCONVERSION PROCESS USING LIQUID PHASE HAVING TO ENHANCE GAS PHASE CONVERSION

(75) Inventors: Rathin Datta, Chicago, IL (US); Shih-Perng Tsai, Naperville, IL (US); Jian Xu, Lisle, IL (US); Seong-Hoon Yoon, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 788 days.

This patent is subject to a terminal disclaimer.

(21) Appl. No.: 12/258,193

(22) Filed: Oct. 24, 2008

(65) Prior Publication Data

US 2010/0105116 A1 Apr. 29, 2010

(51) Int. Cl.
*C02F 3/34* (2006.01)
*A62D 3/00* (2007.01)
*A62D 3/02* (2007.01)
*C12P 7/06* (2006.01)

(52) U.S. Cl. ........ 435/262; 435/161; 435/140; 435/141; 435/160; 435/262.5; 435/41; 435/297.1; 210/601; 210/603; 210/605; 210/606

(58) Field of Classification Search .................. 435/161, 435/140, 141, 160, 262, 262.5, 41, 297.1; 210/601, 603, 605, 606

See application file for complete search history.

(56) References Cited

U.S. PATENT DOCUMENTS

| | | | |
|---|---|---|---|
| 4,181,604 A | 1/1980 | Onishi et al. | |
| 4,348,638 A | 9/1982 | Boldridge, Jr. | |
| 4,440,853 A | 4/1984 | Michaels et al. | |
| 4,442,206 A | 4/1984 | Michaels et al. | |
| 4,746,435 A | 5/1988 | Onishi et al. | |
| 4,921,799 A | 5/1990 | Kitaura et al. | |
| 5,116,506 A | 5/1992 | Williamson et al. | |
| 5,173,429 A | 12/1992 | Gaddy et al. | |
| 5,563,069 A | 10/1996 | Yang | |

(Continued)

FOREIGN PATENT DOCUMENTS

WO WO 02/08438 1/2002

(Continued)

OTHER PUBLICATIONS

Datta et al, Reprinted from vol. 24 of Developments in Industrial Microbilogy, a Publication of the Society for Industrial Microbiology—1985, Chapter 10, Anaerobic Bioconversion of One-Carbon Compounds, pp. 1-6.

(Continued)

*Primary Examiner* — Nathan Bowers

(57) ABSTRACT

The bioconversion of gas feedstreams to liquid products by direct contact with a layer of microorganism obtains enhanced productivity through the regular cycling of liquid across a substrate that supports a biolayer of microorganisms while separating the gas and liquid phases. Such processes produce liquid products such as ethanol, butanol and other chemicals from syngas components by contacting CO or a mixture of $CO_2$ and $H_2$ with a highly porous side of an asymmetric membrane under anaerobic conditions and transferring these components into contact with microorganisms contained within bio-pores of the membrane. A periodic laving of liquid from the liquid contact side to and away from the microorganisms can increase nutrient flow to the microorganisms while enhancing the recovery of liquid products. The process effects laving by temporarily raising the liquid phase pressure relative to the gas phase pressure to periodically surge liquid toward the microorganisms and then restoring the original pressure differential to urge liquid away from the microorgaisms.

26 Claims, 6 Drawing Sheets

U.S. PATENT DOCUMENTS

| | | |
|---|---|---|
| 5,753,474 A | 5/1998 | Ramey |
| 6,043,392 A | 3/2000 | Holtzapple et al. |
| 6,136,577 A | 10/2000 | Gaddy |
| 6,340,581 B1 | 1/2002 | Gaddy |
| 6,387,262 B1 | 5/2002 | Rittmann et al. |
| 6,558,549 B2 | 5/2003 | Cote et al. |
| 6,599,348 B2 | 7/2003 | Chosnek et al. |
| 6,908,547 B2 | 6/2005 | Cote et al. |
| 6,919,488 B2 | 7/2005 | Melnichuk et al. |
| 7,118,672 B2 | 10/2006 | Husain et al. |
| 7,169,295 B2 | 1/2007 | Husain et al. |
| 7,189,323 B2 | 3/2007 | Lofqvist et al. |
| 7,285,402 B2 | 10/2007 | Gaddy et al. |
| 7,300,571 B2 | 11/2007 | Cote et al. |
| 2005/0054087 A1 | 3/2005 | Cote et al. |
| 2006/0021936 A1 | 2/2006 | Husain et al. |
| 2006/0037896 A1 | 2/2006 | Cote et al. |
| 2006/0096918 A1 | 5/2006 | Semmens |
| 2006/0117955 A1 | 6/2006 | Cranford et al. |
| 2006/0141636 A1* | 6/2006 | Steggles et al. ............... 436/177 |
| 2006/0163157 A1 | 7/2006 | Cote et al. |
| 2008/0044850 A1* | 2/2008 | Taylor et al. .................... 435/41 |
| 2008/0305539 A1 | 12/2008 | Hickey et al. |
| 2009/0029434 A1 | 1/2009 | Tsai et al. |
| 2009/0035848 A1 | 2/2009 | Hickey |
| 2009/0104676 A1 | 4/2009 | Tsai et al. |
| 2009/0215022 A1* | 8/2009 | Page et al. .......................... 435/3 |
| 2009/0215139 A1 | 8/2009 | Datta et al. |
| 2009/0215142 A1 | 8/2009 | Tsai et al. |
| 2009/0215153 A1 | 8/2009 | Tsai et al. |
| 2009/0215163 A1 | 8/2009 | Tsai et al. |
| 2009/0286296 A1 | 11/2009 | Hickey et al. |

FOREIGN PATENT DOCUMENTS

| | | |
|---|---|---|
| WO | WO2008154301 | 12/2008 |

OTHER PUBLICATIONS

Kim et al, Plant Cell Immobilization in a Dual Hollow Fiber Bioreactor, Biotechnology Techniques vol. 3 No. 2, 1989, pp. 139-144, Received as revised Jan. 30.

Inloes, D. S, et al, Hollow-Fiber Membrane Bioreactors Using Immobilized *E. coli* for Protein Synthesis, pp. 2653-2681.

Inloes, D. S. et al, Ethanol Production by *Saccharomyces cerevisiae* Immobilized in Hollow-Fiber Membrane Bioreactors, Received Apr. 11, 1983/Accepted Apr. 25, 1983, Applied and Environmental Microbiology, Jul. 1983, vol. 46. No. 1, pp. 264-278.

Henstra, A. M. et al, Microbiology of Synthesis Gas Fermentation for Biofuel Production, ScienceDirect, Current Opinion in Biotechnology 2007, 18:200-206.

Clausen, E.C., et al., "Ethanol From Biomass by Gasification/Fermentation", Presented at Plastics, Tires, Auto Wastes/Biomass MSW Symposium, Fall 1993, Chicago, 38 (3).

Klasson, K.T., et al., "Biological Production of Liquid and Gaseous Fuels from Synthesis Gas," Appl. Biochem. Biotechnol., vol. 24-25, No. 1, Mar. 1990, 857-873.

Vega, J. L., et al., "The Biological Production of Ethanol from Synthesis Gas," Appl. Biochem. Biotechnol. vol. 20-21, No. 1, Jan. 1989, 781-797.

Phillips, John R., et al., "Synthesis Gas as Substrate for the Biological Production of Fuels and Chemicals," Appl. Biochem. Biotechnol. vol. 45-46, No. 1, Mar. 1994, 145-157.

Barik, S., et al., "Biological Production of Alcohols from Coal Through Indirect Liquefaction," Appl. Biochem. Biotechnol. vol. 18, No. 1, Aug. 1988, 363-387.

\* cited by examiner

BIOCONVERSION PROCESS USING LIQUID PHASE HAVING TO ENHANCE GAS PHASE CONVERSION

FIELD OF THE INVENTION

This invention relates to the biological conversion of gas streams using microorganisms to produce liquid products.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

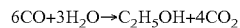

$$6CO + 3H_2O \rightarrow C_2H_5OH + 4CO_2$$

$$6H_2 + 2CO_2 \rightarrow C_2H_5OH + 3H_2O$$

Thus 6 moles of relatively insoluble gases such as CO or $H_2$ have to transfer to an aqueous medium for each mole of ethanol. Other products such as acetic acid and n-butanol have similar large stochiometric requirements for the gases.

Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance. To get high yields and production rates the cell concentrations in the bioreactor need to be high and this requires some form of cell recycle or retention.

Cell retention by formation of biofilms is a very good and often inexpensive way to increase the density of microorganisms in bioreactors. This requires a solid matrix with large surface area for the microorganisms to colonize and form a biofilm that contains the metabolizing microorganisms in a matrix of biopolymers that the microorganisms generate. Trickle bed and some fluidized bed bioreactors make use of biofilms to retain microorganisms on solid surfaces while providing dissolved gases in the liquid by flow past the solid matrix. They suffer from either being very large or unable to provide sufficient gas dissolution rates.

Particular forms of membranes have found use in supporting specific types of microorganisms for waste water treatment processes. U.S. Pat. No. 4,181,604 discloses the use of hollow fiber membranes for waste treatment where the outer surface of the fibers supports a layer of microorganisms for aerobic digestion of sludge.

U.S. Ser. No. 11/781,717 filed Jul. 23, 2007, U.S. Ser. No. 11/833,864 filed Aug. 3, 2007 and U.S. Ser. No. 11/972,454 filed Jan. 10, 2008 disclose a membrane based bioreactor wherein anaerobic bacteria that have the ability to convert syngas to ethanol or other liquids have formed biofilms on the outer surface of hydrophobic membranes with the syngas fed to the bacterial biofilm through the inner surface of the membrane. Such a bioreactor system has been able to directly convert the primary components of synthesis gas, CO and $H_2/CO_2$, to ethanol and other liquid products such as n-butanol, acetic acid and butyric acid. In these systems the gas flows through a porous region of a hydrophobic membrane and then reaches a biofilm which is hydrophilic. One drawback of this arrangement is that if water reaches and deposits/condenses on the hydrophobic porous region it will severely decrease the gas transfer rate. Since the biofilm grows on the outside of the membrane, this type of membrane system also lacks a direct means to promote the formation of a biofilm with an adequate thickness and control its performance.

Asymmetric membranes are known for use in a variety of membrane separations processes such as ultra and nano filtration. Asymmetric membranes are typically hydrophilic and have a relatively tight semi permeable "skin" layer on one side supported on a porous polymer layer. U.S. Pat. Nos.

4,442,206 and 4,440,853 show the use of the polymer layer in an asymmetric membrane to immobilize microorganisms for certain biological processes that use soluble carbon sources. However, the adaptation and use of such membranes for the anaerobic bioconversion of syngas to liquids has not been shown in the past.

SUMMARY OF THE INVENTION

It has been found that microorganisms can directly feed on a gaseous stream by growing the microorganisms in direct contact with a gaseous phase as a biolayer on or within the surface of a substrate such as membrane while permeating liquid containing nutrients across the substrate from its opposite side and into contact with the to the biolayer while liquid products concurrently flow back to the membrane liquid phase for recovery. It has further been found that causing periodic pulsing of the liquid phase in greater quantity toward the biolayer through a laving cycle will improve the production of desired liquid products by the microorganisms.

U.S. Ser. No. 12/036,007 filed Feb. 22, 2008 discloses a suitable arrangement for the application of this invention by inclusion of a laving cycle. The disclosed arrangement retains a biolayer on an asymmetric membrane to contain anaerobic microorganisms for converting syngas (herein defined to include any gas containing CO and/or a mixture of $CO_2$ and $H_2$ as its principal components). This type of arrangement will provide a stable system for enhancing the production of liquid products such as ethanol, butanol, hexanol, and other chemicals from a syngas stream. In this arrangement a porous side of the asymmetric membrane, referred to herein as a bio-layer provides pores also referred to as biopores that promote and control the growth of microorganism colonies therein while also exposing a surface over which to directly feed the microorganisms with syngas. Simultaneously another layer of the asymmetric membrane having less permeability than the bio-layer, herein referred to as a hydration layer, permeates liquid from the opposite side of the asymmetric membrane. Applying the process of this invention to this arrangement would require periodic increase in the relative pressure of the liquid side to the gas phase side to thereby cause a temporary increase in the liquid concentration in and about the biolayer.

In general the asymmetric membrane provides a multi-layer membrane structure having a highly porous bio-layer for retaining the microorganisms within its pores and one or more hydration layers for controlling the supply of water to and from the bio-layer. In its operation syngas contacts one side of the asymmetric membrane through the bio-layer while a nutrient and product containing liquid contacts the other through the hydration layer. Either the bio-layer or hydration layer may comprise multiple layers. The bio-layer, the hydration layer and/or additional layers may also serve to occlude pore openings, extract products, and supply water and nutrients within the bioreactor system. The result is a highly efficient and economical transfer of the syngas at essentially 100% utilization, overcoming limitations for the other fermentation methods and fermentor configurations.

In the case of syngas fermentation with the asymmetric membrane, carbon monoxide or hydrogen/carbon dioxide from the syngas diffuses into the bio-layer and contacts the immobilized microorganisms in the porous membrane wall that convert the syngas into ethanol or other water-soluble products. The water soluble products diffuse into the aqueous stream flowing over the hydration layer and get carried out of the bioreactor. The immobilized microorganisms remain hydrated through contact with the aqueous stream as it passes through the hydration layer.

The process of this invention enhances the diffusion of the liquid products and the hydration of the microorganisms across the membrane by cyclically pulsing nutrient containing liquid toward the microorganisms and then allowing the liquid to permeate back toward the liquid contact surface of the membrane. This laving action of periodically shifting the liquid gradient through the membrane moves liquid to and from the biolayer for improved nourishing of the microorganisms and allows maintenance of desired product concentrations.

Accordingly a broad description of this invention is a process for converting a feed gas using a bioreactor containing microorganisms to produce a liquid product wherein a liquid permeable substrate partitions the microorganisms from liquid phase, retains the microorganisms in direct contact with the gas phase to produce the liquid product and delivers the liquid product to a liquid phase on the side of the substrate opposite the gas phase, said process comprising. The process includes the steps of passing the feed gas to a substrate having a gas contacting side in contact with the feed gas that retains a bio-layer of microorganisms and passing a liquid phase over a liquid contacting side of substrate comprising a hydration layer that controls the flow of product containing liquid from bio-layer. The process maintains sufficient pressure on the gas contacting side to establish a differential pressure between the gas contacting side and the liquid contacting side sufficient to transport the feed gas and the liquid products in co-directional flow from the gas contacting side to the liquid contacting side for a limited period of time. Periodically the process subjects the bio-layer to a laving cycle by reducing the first differential pressure such that liquid from the liquid contacting side laves into the biolayer.

In another form the process of this invention converts a feed gas using a bioreactor containing microorganisms to produce a liquid product and delivers the liquid product to a product containing liquid. The process passes the feed gas to a plurality of modules each containing an asymmetric hydrophilic membrane having a gas contacting side in contact with the feed gas, a bio-layer defining a plurality of bio-pores having effective diameters of at least 1 μm over at least a portion of the pore length for retaining microorganisms therein, and a porous surface on the bio-layer defining the gas contacting side that presents open ends of the bio-pores to the feed gas. A liquid phase passes to the plurality of modules and in each module the liquid contacts a liquid contacting side of the asymmetric hydrophilic membrane comprising a hydration layer that provides a controlled flow of product containing liquid from the bio-layer into the liquid phase to supply the product containing liquid. The process maintains sufficient pressure on the gas contacting side in at least a portion of the modules to transport the feed gas and the liquid products in co-directional flow from the gas contacting side to the liquid contacting side.

Periodically the process subjects the bio-layer in a portion of the modules to a laving cycle in which liquid from the liquid contacting side laves into the biopores by creating a pressure differential wherein the pressure on the gas contacting side is lowered from its normal pressure. The relative pressure reduction on the gas side will vary but any reduction that increases the liquid concentration in the biopores will effect laving. Generally during laving the pressure on the gas side will approximately equal the pressure on the liquid contacting side. The process sequentially changes the modules that are subjected to the laving cycle.

A further description of the invention is a process for converting a feed gas using a bioreactor comprising a plurality of membrane modules containing microorganisms to produce a liquid product and delivering the liquid product to a product containing liquid. The process passes the feed gas to a plurality of modules each containing an asymmetric hydrophilic hollow fiber membrane having an outer surface defining a gas contacting side in contact with the feed gas, a bio-layer defining a plurality of bio-pores having effective diameters of at least 1 µm over at least a portion of the pore length for retaining microorganisms in the biopores, and a porous surface on the bio-layer defining the gas contacting side that presents open ends of the bio-pores to the feed gas. A product containing liquid passes to the plurality of modules and in each module the liquid passes over a liquid contacting side defined by the lumen of the asymmetric hydrophilic membrane. A hydration layer borders the lumen to controls the flow of product containing liquid from bio-layer and define the liquid contact side of the membrane. The process maintains sufficient pressure on the gas contacting side of the modules to transport the feed gas and the liquid products in co-directional flow from the gas contacting side to the liquid contacting side. Periodically the process laves the bio-layer in a at least a portion of the modules with a laving cycle by decreasing the pressure of the gas contacting side relative to the liquid contacting side so that liquid from the liquid contacting side laves into the biopores. Periodically the process purges the biolayer in at least one of the modules with a purge cycle wherein the pressure on the liquid side of the membrane exceeds the pressure on the gas side of the membrane by a sufficient amount such that liquid flows from the liquid contacting side and out of the biopores onto the gas contacting side to flush microorganisms and/or extra cellular material from the bio-pores. The process alternates the modules that are subjected to the laving cycle and the purge cycle so that all of the modules periodically undergo laving and purging.

DETAILED DESCRIPTION OF THE INVENTION

Figure 1:
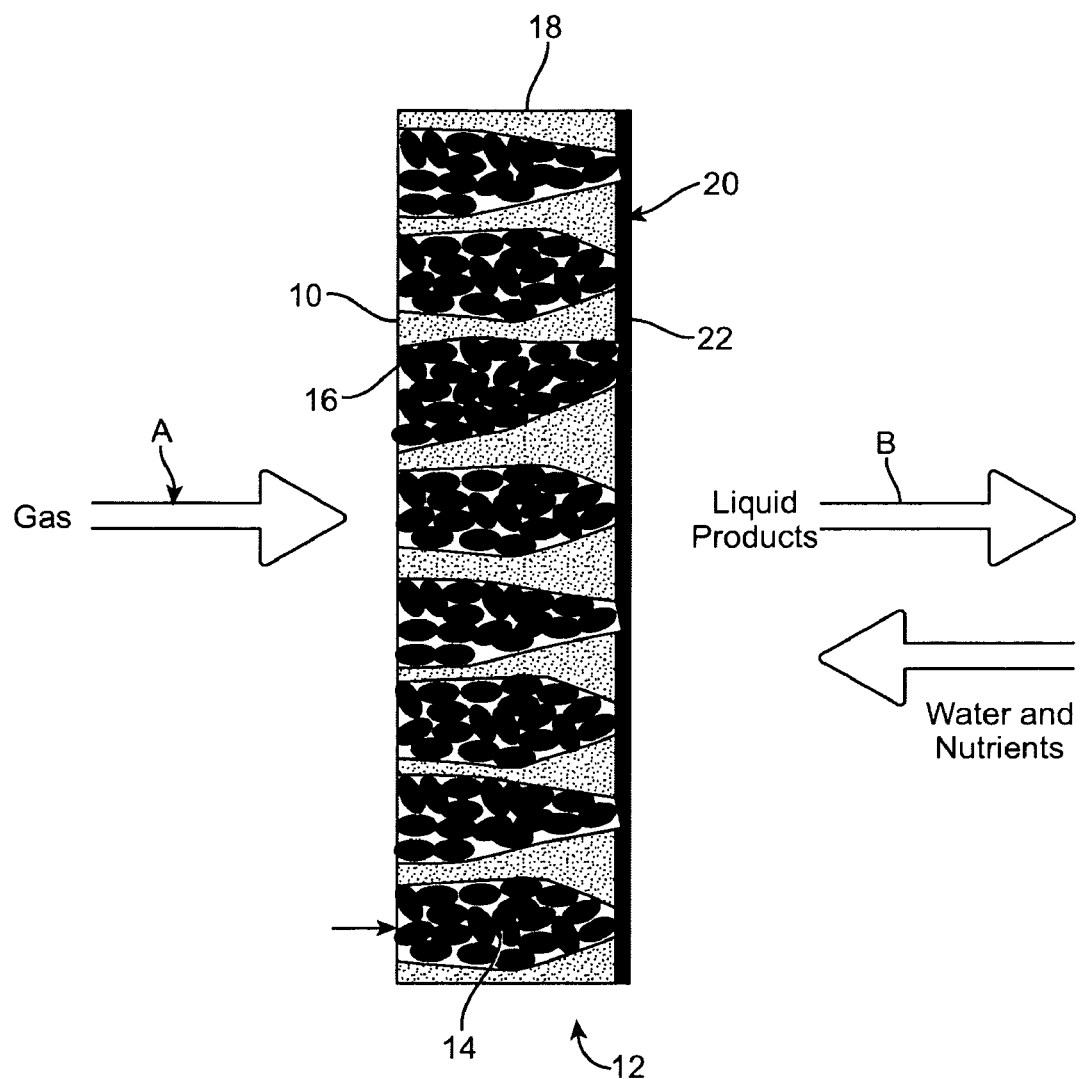
FIG. 1 is a schematic drawing showing a cross section of an asymmetric membrane with gas stream in contact with a bio-layer that retains microorganisms therein and a hydration layer in the form of a skin in contact with liquid.

While the use of this invention applies initially to the conversion of syngas to make liquid products therefrom, this invention can find application to any process or apparatus that retains a microorganism in a gas contacting side of a permeable substrate and requires permeation of liquid to and from the microorganism from the opposite side of the permeable substrate. The permeable substrate may comprise any material with a suitable surface to retain the microorganisms in a gas contacting side and permeate liquid at controlled rates across its thickness. A variety of membrane materials may serve as substrates including ceramics, sintered elements and various polymers. The substrates may comprise a single layer of the same material, multiple layer of the same material or multiple layer of different materials.

In its preferred form the substrate provides a porous surface upon and in which the microorganisms colonize as a biolayer as disclosed U.S. Ser. No 12/036,007. The asymmetric membrane typically places one or more less porous hydration layers opposite the gas contacting side establish an interface to provide water and trace nutrients that travel from the liquid toward the microorganisms contained in the biopores of the biolayer while simultaneously extracting liquid products from the microorganisms. The extracted liquid flows across the hydration layer and into the liquid medium. Thus the desired products and the syngas from which they are produced flow through the layers of the membrane in the same direction, from the highly porous bio-layer to the less porous hydration layer. The liquid that contacts the less porous layer circulates over the membrane's liquid contacting surface and out of the bioreactor to facilities for the removal of the desired products.

The bio-pores of the bio-layer retain microorganisms for the production of the products from the syngas. The bio-layer keeps the microorganisms concentrated in bio-pores while still in direct contact with the syngas through a gas contacting side of bio-layer thereby keeping syngas components readily available to enhance production of ethanol and other soluble products by the retained microorganisms. The microorganisms may reside in the bio-layer in isolation or as a biofilm. Some protrusion of the microorganisms outside of the bio-pores and past the gas contacting surface will not stop the operation of the bioreactor system. Slight outgrowth of the microorganisms does not plug the gas flow path. Desirably however, the thickness of the bio-layer will dictate the thickness of any biofilm or colony of microorganisms so that the microorganisms fill up the bio-pores to the surface level of the bio-layer's gas contacting side. This permits pre-engineering of the microorganisms into a layer with a thickness that matches the thickness of the bio-layer wall. It also provides the added advantage of keeping microorganisms well confined and preventing their catastrophic loss.

Confinement works well with the microorganisms that are used for such anaerobic bioconversion of syngas components. These microorganisms grow slowly, produce product at the stationary phase and do not produce excess gas. Thus they are particularly suitable of use in the bio-pores because they will not destroy the membrane.

The bio-layer provides significant advantages in the utilization of syngas. Retaining the microorganisms in the bio-pores provides direct contact and gas transfer with the syngas. This eliminates any gas transfer resistance through a non-porous membrane layer or from wetting of the membrane pores.

Placing the hydration layer between the microorganisms and the liquid simplifies the operation of downstream separation facilities. The hydration layer provides a substantial barrier between the microorganisms and the product containing liquid that keeps the liquid flowing to separation facilities free of microorganisms, extra cellular material and other biological contaminants. Extra cellular material may include cell debris, biological polymers and other precipitates. Eliminating biological contaminants extra cellular material from the liquid effluent removes the need for filtering and/or recycling of such materials.

The asymmetric membrane may be formed from any material or assemblage of materials that provide a bio-layer and a hydration layer with the functionality as described. In one form the bio-layer comprise hydrophilic materials that readily supply water throughout the bio-pores and up to the surface of the bio-layer's gas contacting side. The use of hydrophilic materials for the less porous hydration layer will enhance performance of the membrane by allowing easy movement of the water through the membrane. In many instances the bio-layer and the hydration layer will comprise the same material with the hydration layer taking the form of a skin on one side of the asymmetric membrane. A hydration layer comprising a skin layer will normally also occludes the bio-pores to prevent migration of microorganisms into the liquid medium.

Utilization of the asymmetric membrane in this manner permits the bioreactor system to take on a variety of configurations. For example the asymmetric membrane may comprise hollow fibers or flat sheets whether in flat or spiral wound configurations. Suitable hollow fiber membranes may place the bio-layer or the hydration layer on the lumen side. Suitable housings may retain the membrane for co-current, counter-current, or cross-flow with respect to the circulation of the liquid on one side of the membrane and the bulk gas flow on the opposite side. In the case of hollow fibers, the bioreactor may work well whether extending in a principally horizontal or vertical direction.

This invention also improves operations for the circulation of liquid on the lumen side of hollow membranes by providing a well defined liquid flow path and providing a contiguous space for gas flow on the outside of the membrane. This permits very high density packing of the asymmetric membrane elements without fear of disrupting liquid flow patterns and creating stagnant areas for the circulating fluid. As a result the bioreactor system requires an overall smaller working volume than other proposed systems for conversion of syngas by fermentation.

Bioconversions of CO and $H_2/CO_2$ to acetic acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) and this will enable the production of ethanol as well as acetic acid. All of these references are incorporated herein in their entirety.

The microorganisms found most suitable thus far for this invention require anaerobic growth conditions. Therefore bioreactor arrangement will usually employ control and sealing methods to limit the introduction of oxygen into the system. Since the microorganisms contact the liquid that circulates through the bioreactor system, a suitable redox potential will be maintained and monitored to insure anaerobic conditions. Anaerobic conditions in the liquid volume are usually defined as having a redox potential of less than −200 mV and preferably a redox potential in the range of from −300 to −500 mV. To further minimize exposure of the microorganisms to oxygen, the feed gas will preferably have an oxygen concentration of less than 1000 ppm, more preferably less than 100 ppm, and even more preferably less than 10 ppm.

The invention can use asymmetric membranes having a porous layer and a less permeable layer. The porous layer, referred to as the bio-layer may comprise any material suitable for the formation of the bio-pores and the transport of liquid to and away from the microorganisms in the bio-pores. The less porous layer, referred to as the hydration layer will control the transport of the fermentation liquid to and from the bio-layer for nourishing the microorganisms and maintain effluent products at desired concentrations. The bio-layer and hydration layer are described as single layers but either may comprise several layers.

The asymmetric membrane also requires material that will provide support to the membrane structure and will occlude the internal end of the bio-pores to prevent microorganisms and extra cellular material from passing into the fermentation liquid. The asymmetric membrane may contain additional layers for internal support and formation of the bio-pores or the bio-layer and/or hydration layer may serve these functions as well. Any additional layers must permit direct contact of syngas with the microorganisms in the bio-pores and the permeation of liquid into the bio-layer.

The bio-layer defines the bio-pores for retaining the microorganisms in direct contact with the syngas. The biopores typically have an effective diameter of at least 1 μm over at least a portion of its length. The term effective diameter refers to the open cross-sectional area of a regularly shaped pore that would provide the same cross sectional area. The pores need not have a uniform cross section and bio-pores having an effective diameter of 1 μm over at least a third of its length will work well. The size of the bio-pores in the bio-layer of the membrane will usually have an effective diameter substantially greater than 1 μm, preferably in the range of 2 to 100 μm, and most preferably in the range of 5 to 50 μm. Typical depths of the bio-pores range from 50 to 500 µm which generally corresponds to the thickness of the bio-layer.

At minimum the hydration layer restricts the liquid permeability with respect to the biolayer. The restricted permeability prevents excessive fermentation liquid from migrating into the bio-layer during normal operation of the system and interfering with contact between the gas and microorganisms. In most cases the hydration layer will comprise a higher density material than the bio-layer that restricts liquid flow while also occluding the internal end of the bio-pores to block migration of the microorganisms into the fermentation liquid.

Particularly suitable forms of asymmetric membranes are porous membranes with a tight (i.e., having small pores) thin "skin" on one surface of the membrane that provides the hydration layer and a relatively open support structure underneath the skin that provides the bio-layer and defines the bio-pores. The skin will typically comprise a semi-permeable layer having a thickness of from 0.5 to 10 μm. The skinned asymmetric membrane can include an "integrally skinned" membrane prepared by using phase inversion of one polymer or a composite membrane, where a thin layer of a certain material is formed on top of a porous sublayer of a same or different material. General description of asymmetric membranes and methods of their preparation can be found in the literature (e.g., Cheryn, M., Ultrafiltration and Microfiltration Handbook, Technomics Publishing Company, Lancaster, Pa., 1998; and Mulder, M., Basic Principles of Membrane Technology, $2^{nd}$ Edition, Kluwer Academic Publishers, Norwell, Mass., 1996).

A suitable skin layer has a pore size that is smaller than the size of microbial cells to prevent the cells from passing through the membrane skin but the opposite surface of the membrane has large openings that allow cells to enter and leave the bio-pores of the membrane wall. Typically, the pore size of the skin layer is less than 0.5 μm, preferably less than 0.25 μm, and most preferably in the ultrafiltration range of nominal MWCO of 10 to 300 kDa and more preferably in the range of 10 to 100 kDa.

Several asymmetric ultrafiltration membranes are available from Millipore Corporation (Bedford, Mass.), including but not limited to the Amicon Membranes and the Ultracel PLC Membranes. The Amicon Membranes are made of polyethersulfone and with a range of a nominal MWCO, for example a nominal MWCO of 30 kDa for Amicon PM30. The Ultracel PLC Membranes, which are composite membranes made from casting the regenerated cellulose membrane onto a microporous polyethylene substrate, are available in the pore size range from 5 kDa (PLCCC) to 1000 kDa (PLCXK). Additional examples of asymmetric membranes are the MMM-Asymmetric Super-Micron Membranes and BTS Highly Asymmetric Membranes, both available from Pall Corporation (East Hills, N.Y.). The MMM-Asymmetric Membranes, available in pore size range from 0.1 to 20.0 μm, are made of polysulfone and polyvinylpyrrolidone. The BTS Highly Asymmetric Membranes, available in pore size range from 0.05 to 0.80 μm, are cast of polysulfone with a "cut off" layer of about 10 μm and a total thickness of about 120 μm.

Hollow fiber membrane modules containing asymmetric ultrafiltration membranes are commercially available from a number of membrane manufacturers. For example, the Kros-Flo® Max Module Model KM5S-800-01N from Spectrum Laboratories (Rancho Dominguez, Calif.) has 22.0 $m^2$ membrane surface area of asymmetric polysufone hollow fiber membranes with 0.5 mm fiber inner diameter, a tight skin on the lumen side, and a pore rating of 50 kDa. ROMICON® polysulfone hollow fiber membranes available from Koch Membrane Systems (Wilmington, Mass.) are also asymmetric with the tight skin on the lumen side. ROMICON cartridge Model HF-97-43-PM50 is a 6-inch module containing fibers of 1.1 mm inner diameter and 50 kDa nominal MWC at 9.0 $m^2$ total membrane surface area.

The asymmetric membrane may also take the form of a composite substrate comprising a semi-permeable skin layer of one material as the hydration layer over a porous substrate such as a very fine mesh or cloth of the same or another material to provide the biopore layer The two layers may be joined by thermally fusing or any other method that will maintain the integrity of the composite structure.

Membranes of the various geometries and compositions described above may be used in arrangements of unitary arrays or assemblies of varied composition in the systems of this invention. Any suitable potting technique can be used to collect and provide the necessary assembly of individual membrane elements. In such membranes the gas and liquid can be brought into direct and intimate contact at the gas contact surface of the bio-layer. Liquid is passed in the liquid side of the membranes via pumping, stirring or similar means to remove the ethanol and other soluble products formed; the products are recovered via a variety of suitable methods.

The syngas flows through the gas chamber or channels of the bioreactor system continuously or intermittently. The feed gas pressure is in the range of 1 to 1000 psig, preferably 5 to 400 psig, and most preferably 10 to 200 psig. The differential pressure between the liquid and gas phases is managed in a manner that the membrane integrity is not compromised (e.g., the burst strength of the membrane is not exceeded) and the desired gas-liquid interface phase is maintained.

The gas side pressure is normally slightly higher than the liquid pressure to prevent convective liquid flow from the hydration layer (liquid) side to the open surface (gas) of the gas contacting side. The higher pressure also avoids formation of a liquid layer at the cell/gas interface, which would impede gas transfer to the cells.

When the feed syngas contains moisture, condensation of water can occur at the microorganism/gas interface as consumption of syngas results in supersaturation of water. This condensed water leaves the cell/gas interface by dripping to the bottom of the bioreactor due to gravity as well as by convective flow through the membrane due to the slightly higher pressure of the gas.

FIG. 1 is a schematic drawing showing a cross-section of an asymmetric membrane with a gas stream in contact with a biolayer that retains microorganisms therein and a hydration layer in the form of a skin in contact with liquid. An asymmetric membrane, suitable for permeation of the fermentation liquid, provides separation between the liquid phase and feed gas comprising at least one of CO or a mixture of $H_2$ and $CO_2$. FIG. 1 shows detail of the membrane configuration and interface in the operation of a representative bioreactor system. FIG. 1 depicts a cross-section of a single membrane element with a syngas stream A flowing to the gas contacting side 10 of the asymmetric membrane 12. The syngas components directly contact the microorganisms 14 contained in biopores 16. An anaerobic acetogenic bacteria, such as *Clostridium ragsdaeli* having all of the identifying characteristics of ATCC No. BAA-622, is maintained in the biopores 16 and is supplied with the fermentation liquid by permeation through the biolayer 18. The fermentation liquid circulates on the opposite side of the syngas stream A and permeates through a hydration layer formed as skin 20 on the inner surface of biolayer 18. Direct contact of the skin 20 with the biolayer 18 transfers the fermentation liquid to the biopores 16. The surfaces of biolayer 18 that contact the microorganisms and gas stream provide equilibrium partitioning across the asymmetric membrane to keep the liquid and gas phases separated from each other. The pores in the skin 20 are much smaller than the width of the microorganisms retained in the biopores 16 so that the skin 20 occludes the inner end of the biopores 16 and prevents the microorganisms from passing through the skin 20 and to liquid contacting surface 22. As a result, the microorganisms 14 preferentially stay within the biopores 16 to gain metabolic energy by converting CO and $H_2/CO_2$ thereby growing and sustaining themselves within the biopores 16. A portion of liquid B is withdrawn and separated to recover the desired products from the fermentation liquid.

To load the asymmetric membrane with microorganisms, the bio-layer first is inoculated with microorganisms followed by further cell growth to reach the desired cell loading density. To inoculate the bio-layer, an aqueous solution containing microorganisms is introduced to the gas contacting side of the asymmetric membrane, and then the solution is slowly filtered through the bio-layer and hydration layer by applying a slight trans-membrane pressure, creating a microorganism-free filtrate through the hydration layer and entrapping cells within the bio-pores of the bio-layer. The microorganism-containing membrane is incubated for further microorganism growth, by contacting the membrane with a liquid solution containing nutrients and carbon source suitable for microorganism growth. Alternatively, the membrane can be incubated using a syngas and a liquid solution containing nutrients.

Figure 2:
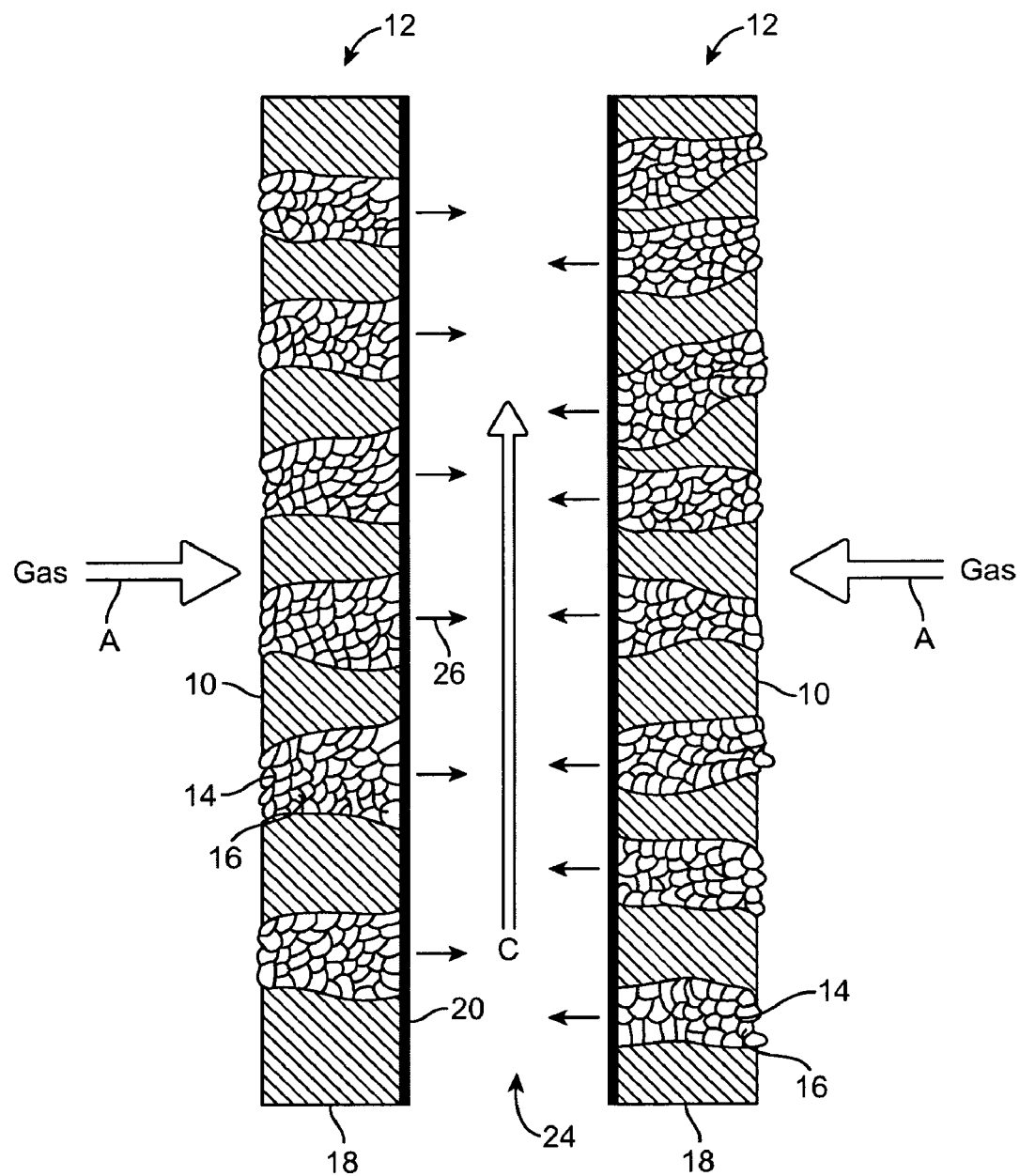
FIG. 2 is a schematic drawing showing a central passage formed by two membranes of the type shown in FIG. 1 with a gas stream contacting the outer wall and liquid contacting the inner walls.

FIG. 2, in which like elements share like reference numbers with FIG. 1, is a schematic drawing showing a central passage formed by two membranes of the type shown in FIG. 1 with a gas stream contacting the outer wall and liquid contacting the inner walls. Two asymmetric membranes 12 border a central liquid channel 24 through which a fermentation liquid circulates in the direction of stream C. The asymmetric membranes 12 on each side of liquid channel 24 function in a similar manner to that described for the single membrane element of FIG. 1. Syngas flows across gas contacting side 10 into contact with the microorganisms 14 and fermentation products pass out the skin 20 in the direction of arrows 26. The arrangement of FIG. 2 can use a flat sheet configuration or a tubular configuration and be particularly useful for good flow control and distribution on the liquid side.

The gas side and the liquid side may operate at any pressure that best suits the particular conversion and provide the most productive environment for the microorganisms. The feed gas pressure and the pressure on the gas and the liquid side will usually range from is in the range of 0.1 to 100 bars, preferably 0.3 to 30 bars, and most preferably 0.7 to 15 bars. The pressure differential between the gas and the liquid side will determine the liquid gradient through the membrane and the concentration of liquid in and about the biolayer. Differential pressure between the gas side and the liquid side will usually not exceed 3 bars and more typically not exceed 1 bar. In the most operations, the gas contacting side 10 is maintained at higher pressure than the pressure of the liquid that contacts skin 20 to promote gas transfer and prevent convective liquid flow from the hydration layer (liquid) side to the open surface (gas) of the gas contacting side.

To effect laving, one may temporarily elevate the pressure on the liquid side relative to the gas side such until the concentration of liquid in and about the biolayer increases. Another way to effect laving, periodically reduces the gas pressure to a value approximately equal to the liquid pressure for a finite duration. In either case the laving cycle ends as the pressure differential returns back to the normal value and the liquid gradient through the biolayer returns to the approximately the pre-laving state. The changes of the differential pressure during the laving cycle facilitate the movement of the fermentation liquid to and from the bio-layer for nourishing the microorganisms and maintaining the effluent products at desired concentrations.

The frequency and duration of the laving cycles will, among other factors depend on the gas feed composition, the type of products produced, the characteristics of the liquid stream, the make-up of the substrate (membrane) and the nutrient and water requirement of the microorganisms. In most conversions the laving cycle will occurs at a frequency of 10 seconds to 20 minutes and the duration of the laving cycle will last from 0.5 seconds to 10 minutes. In some cases, particularly for asymmetric membranes, the laving cycle may occur at frequency of 2 to 15 minutes and for a duration of 10 seconds to 10 minutes. In most cases laving should end before any liquid phase accumulates on the surface of the biolayer since the presence of a liquid at the gas interface limits the gas transfer capacity of the biolayer with the microorganisms. In typical practice the laved liquid remains within the biopores during the laving cycle.

Figure 3:
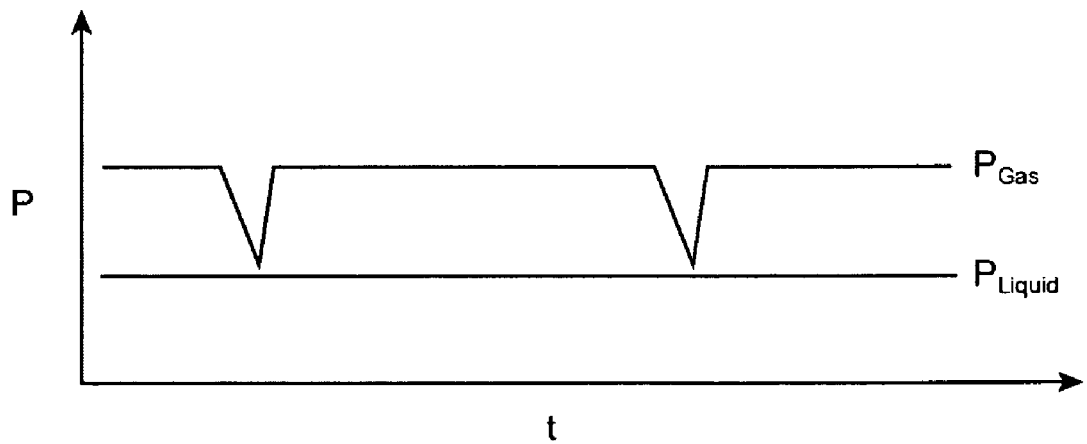
FIG. 3 is a graph illustrating relative gas and liquid phase pressures during laving cycles.

One way to reduce pressure on the gas contacting side and effect laving is to restrict or stop the flow of gas to the contacting side. FIG. 3 illustrates a graph of relative gas and liquid phase pressure for a membrane bioreactor that undergoes multiple laving cycles. As the gas consumption and escape of gas continues, the pressure drops with the reduction in feed gas partial pressure and the laving begins. Pressure drop continues until the liquid phase advances to the desired degree across the thickness of the membrane wall that provides the biolayer. Restoring the feed gas supply completes the laving cycle by bringing the gas side pressure back to a normal level.

Figure 4:
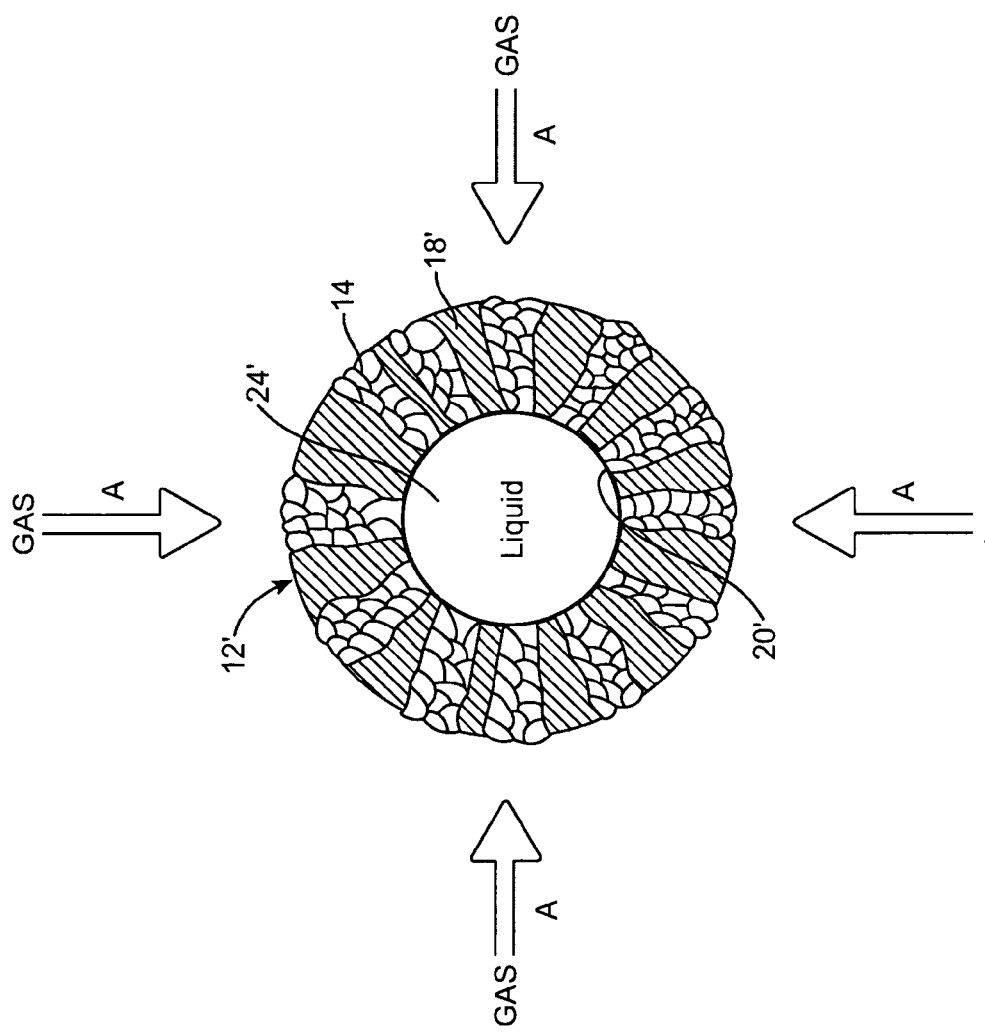
FIG. 4 is a schematic drawing showing a transverse cross-section of the asymmetric membrane made into a hollow fiber with the bio-layer on the outside and the hydration layer on the inside.

FIG. 4 is a schematic drawing showing a transverse cross-section of the asymmetric membrane of FIGS. 1 and 2 made into a hollow fiber with the biolayer on the outside and the hydration layer on the inside. FIG. 3 shows a special case of FIG. 2 wherein the asymmetric membrane 12' wraps around in continuous form to provide a tubular membrane with a central liquid channel 24'. In this case the syngas stream A flows radially inward into contact with the microorganisms 14 contained within an annular biolayer 18'. The skin 20' covers the inner surface of the biolayer 18' and controls the permeation of liquid across biolayer 18'.

Figure 5:
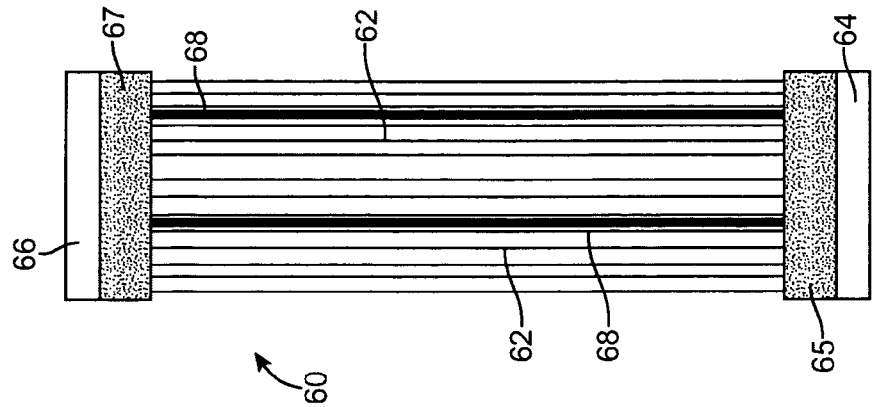
FIG. 5 shows a module arrangement for arranging asymmetric membrane elements as an assembly of multiple hollow fiber elements.

FIG. 5 is a schematic drawing of a two-headed membrane module for use in a bioreactor system with gas and liquid circulation. Each membrane module provides a large surface area of asymmetric hydrophilic membranes in the form of hollow fibers. The hollow fibers are oriented vertically. A number of the membrane modules can be located in a closed membrane vessel containing process gas, so that a very large total membrane surface area can be achieved with a small number of membrane vessels, simplifying plant design and reducing costs. The membrane vessel (not shown) can be round, square, rectangular or any other suitable shape and can employ gas-tight cover plates as needed to contain the feed gas. In the arrangement and method of this invention process liquid typically fills the hollow fiber lumens, while a biolayer and process gas are on the shell side of hollow fibers. In one embodiment, the membrane modules can have support structures around the hollow fibers to keep the hollow fibers from collapsing. The membrane modules can have any cross section as desired for a particular purpose, such as round, rectangular, square, or any other cross section that accommodates a desired pitch and/or spacing.

Each of the membrane modules has a number of hollow fibers and each of the hollow fibers has an asymmetric hollow fiber wall defining a hollow fiber lumen and an outer surface. Process gas passes through the hollow fiber wall to interact with the biolayer and generate a liquid product that mixes with the process liquid. Process liquid passes through the hollow fiber wall in the opposite direction to provide water and nutrients to the biolayer. Numerous combinations of syngas and microorganisms can be selected as desired for generating a particular liquid product desired. The process gas can be a synthesis gas (syngas), such as a mix of CO, $H_2$, and $CO_2$ with other components such as $CH_4$, $N_2$, $NH_3$, $H_2S$, and other trace gases, or the like. The biolayer supports a culture, such as *Clostridium ragsdalei, Butyribacterium methylotrophicum, Clostridium ljungdahlii, Clostridium carboxidivorans*, combinations thereof, and the like, which can generate the liquid product from the syngas. The liquid product can be ethanol, n-butanol, hexanol, acetic acid, butyric acid, combinations thereof, and the like, depending on the syngas and culture selected.

FIG. 5 illustrates a two-headed membrane module. The membrane module 60 can include hollow fibers 62 as shown in FIGS. 2 & 4. The hollow fibers 62 define biopores that open to the outer surface of the hollow fibers and contain the biolayer. In this arrangement, the membrane module 60 includes a number of hollow fibers 62, each having a hollow fiber wall defining a hollow fiber lumen and an outer surface. A liquid inlet chamber 64 is operably connected to one end of the hollow fibers 62 through potted end 65 to provide the process liquid to the hollow fiber lumens and a liquid outlet chamber 66 is operably connected to the other end of the hollow fibers 62 through potted end 67 to receive the process liquid from the hollow fiber lumens. The potted end 65 is spaced apart from the potted end 67. The potted end 65 can be operably connected to a liquid supply conduit and the potted end 67 operably connected to a liquid recovery conduit, or vice versa, so the process liquid can flow through the hollow fiber lumens from one potted end to the other.

The hollow fibers 62 can be potted to the liquid inlet chamber 64 and the liquid outlet chamber 66 with an epoxy or the like. A number of support rods 68 connect the liquid inlet chamber 64 and the liquid outlet chamber 66 to provide mechanical strength to the membrane module 60, which must withstand forces caused by weight of the hollow fibers and biolayer, membrane module handling, and the like. The length of the hollow fibers 62 can be greater than the distance between the liquid inlet chamber 64 and the liquid outlet chamber 66 to give the hollow fibers 62 some slack and freedom to move.

Figure 6:
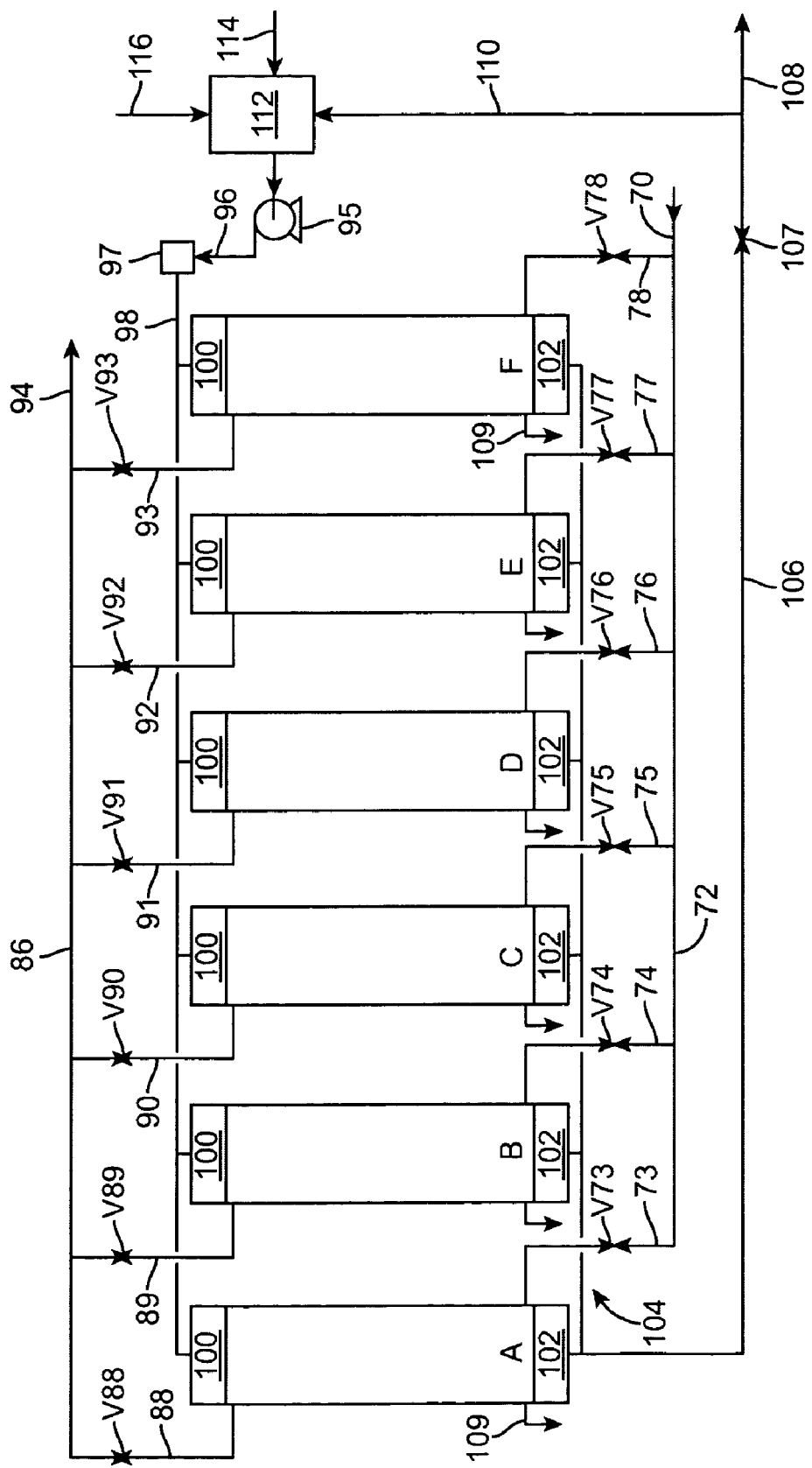
FIG. 6 is a schematic drawing of a bioreactor system showing multiple modules each contained within a separate vessel.

FIG. 6 shows an arrangement for circulation of a process liquid and a process gas through membrane modules A, B, C, D, E, and F to effect a bioconversion and periodic laving of the biolayers contained therein. Each module comprises one or more membrane elements that define bio-pores for promoting the growth and maintenance of microorganisms within a biolayer on each membrane. Feed gas flows to the modules from an gas inlet line 70 through a gas inlet manifold 72 to each of modules A-F via gas inlet pipes 73-78 respectively. An gas outlet header 86 collects remaining feed gas components from the modules A-F via gas outlet pipes 88-93 respectively and delivers the gas to outlet 94.

Process liquid circulates through the lumens of hollow fiber membranes provided by each of modules A-F. Pump 95 delivers the process liquid from a tank 112 through a line 96 at a rate measured by flow meter 97 to a liquid inlet piping 98. An inlet chamber in a head 100 of each module distributes the process liquid to the lumen and a corresponding outlet chamber 102 collects process liquid enriched in the desired product from the lumens of each module. Liquid outlet piping collects the liquid and feeds it to liquid return line 106.

The flow rates of the streams in lines 96 and 106 are selected so that there is no significant liquid boundary layer on the liquid side of the membrane that would impede mass transfer near the liquid-facing side of the membrane. The linear velocity of the liquid tangential to the membrane should be in the range of 0.1 to 50 cm/s, preferably 0.5 to 20 cm/s, and most preferably 2 to 10 cm/s.

Feed gas of CO and $H_2/CO_2$ from the syngas is typically utilized. With this feed a gradient for its transport from the gas feed side is created due to biochemical reaction on the membrane liquid interface. This reaction creates liquid fuel or chemicals such as ethanol and acetic acid which diffuse into the liquid and are removed via circulation of the liquid with the hydration layer of the asymmetric membrane. Thus the very large surface areas of the membrane pores are usable for gas transfer to the microorganisms and the product is recovered from the liquid side. Furthermore, the reaction rate, gas concentration gradient and the thickness of the microorganisms can be maintained in equilibrium because the microorganisms will maintain themselves only up to the layer where the gas is available as a result of the inherently slow growth characteristics of the microorganisms that metabolize syngas components.

The membranes can be configured into typical modules as shown as an example in FIG. 5 for hollow fibers. The gas flows in the fine fibers that are bundled and potted inside a cylindrical shell or vessel through which the liquid is distributed and circulated. Very high surface areas in the range of 1000 m2 to 5000 m2 per m3 can be achieved in such modules.

Liquid from line 106 splits into streams 108 and 110. Line 108 transports a portion of the effluent liquid to product recovery for the separation of liquid products. The product recovery section produces a product stream comprising the desired liquid product and a product deficient stream that returns to a liquid tank 112 via line 114.

Depending on the nature of the desired product, there are a number of technologies that can be used for product recovery of the liquid from line 108. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products. In all cases the product recovery step removes the desirable product from stream 108, while leaving substantial amounts of water and residual nutrients in the treated stream, part of which is returned to the bioreactor system via line 114 and liquid tank 112.

The rest of the effluent liquid carried by line 110 enters tank 112 for mixing with the product deficient stream from line 114 and any needed additives that enter the tank via line 116. Means for temperature and pH control for the liquid can be added anywhere along the re-circulating liquid loop, which includes lines 106, 110, and 96 as well as tank 112. Line 116 provides the nutrients needed to sustain the activity of the microorganisms.

A series of valves control the flow gas through modules A-F and operate to sequentially lave each of the modules. Valves V73-V78 control the flow of gas to each of the gas inlet pipes 73-78 and modules A-F respectively. Each module can periodically undergo laving by closing its gas inlet valve and allowing the gas pressure to decay by consumption of the feed gas and/or allowing gas to escape from the module. As long as feed gas continues to pass through the other modules, the back pressure from the on stream modules limit the available gas pressure reduction for the module that remains on stream.

Thus, without some form of flow restriction the maximum pressure reduction in the laved module equals the pressure drop of the gas through the modules that remain on stream.

To increase the gas pressure reduction during laving by more than the pressure drop through the on stream modules, outlet lines 88-93 each have valves V88-93 respectively. Closing the outlet valve as well as the inlet valve for a module permits consumption of the gas to produce further reductions of pressure on the gas side by eliminating back pressure from the other modules. For example to lave module A in this manner both valves V73 and V88 would operate in a closed condition while the remaining valves V74-V78 and V89-V93 remain in an open condition. Laving of module A ends as valves V73 and V88 return to an open condition.

As an alternative to using valves V88-V93 each valve may be replaced with a suitable flow restrictor such as a restriction orifice to create additional pressure drop. This additional pressure drop will reduce the available back pressure from modules that remain in normal operation so that the closing of a single inlet valve (V73-V78) will effect laving of its respective module.

In addition to reducing the pressure of the feed gas, the laving cycle may also begin with an increase in the liquid pressure or a combination of gas phase pressure reduction and liquid phase pressure elevation. Thus laving may also start by increasing the output pressure from the modules through a pressure reduction valve 107 on line 106.

In most operations the bioreactor arrangements will benefit from occasional purging or flushing of the bio-pores and the gas contacting surfaces. While it is possible to flush the gas contact side of the module with an external stream, most operations will purge the biopores with liquid from the liquid contacting side of the module. Purging in this manner will take place by reversing the pressure differential between the gas phase and the liquid phase so that the liquid pressure is greater than the gas pressure by enough of an amount and/or for a long enough time to weep liquid out of the biolayer. This liquid flow across the substrate wall will purge extra cellular material such as accumulated dead microorganisms, other cell debris, biological polymers, and other precipitates out of from the bio-pores and from the gas contacting surface. This water is collected from the gas stream side of the bioreactor. For example modules A-F all include purge drains 109 to drain water from the shell side of the modules. Optionally the purge may be collected and treated for removal of suspended solids and recirculated to the bioreactor system. Liquid may accumulate at the bottom of membrane vessels for the reasons previously described as well as condensation from moisture in the gas and periodic cleaning operations. Line 109 can remove any such liquid and entrained solid matter from the gas phase side of the vessel.

Purging will occur less frequently than laving. The frequency and duration of purging depends also on a number of nature of the operation and the arrangement of the equipment. Typically purging may last anywhere from 10 second to 10 minutes and take place on a frequency of from 24 to 1000 hours.

Usually it is also desirable to completely clean bio-layer by removal of the microorganisms. This process begins with substantially removing the immobilized cells and cleaning the membrane. To do this the gas supply is stopped, and the membrane is cleaned with cleaning solutions in manners similar to typical cleaning of microfiltration and ultrafiltration membranes. For example, the asymmetric membrane is first soaked in a cleaning solution from both sides, e.g. the bio-layer and hydration layer. The cleaning solution is formulated or selected to facilitate solubilization of microorganism and biopolymers. One of such solutions is an aqueous solution containing 2% NaCl and 0.4% NaOH, but many other formulations have been used for membrane cleaning, including some containing surfactants and hydrolytic enzymes. After soaking, the cleaning solution is circulated and a positive trans-membrane pressure is applied from the hydration layer side to create a convective flow through the membrane and flush microorganism and biopolymers out through the gas contacting surface of the bio-layer. The soaking-filtration procedures can be repeated as needed, and different cleaning solutions can be used. After membrane cleaning, the membrane can be used for loading and growing new cells for syngas fermentation again.

Figure 7:
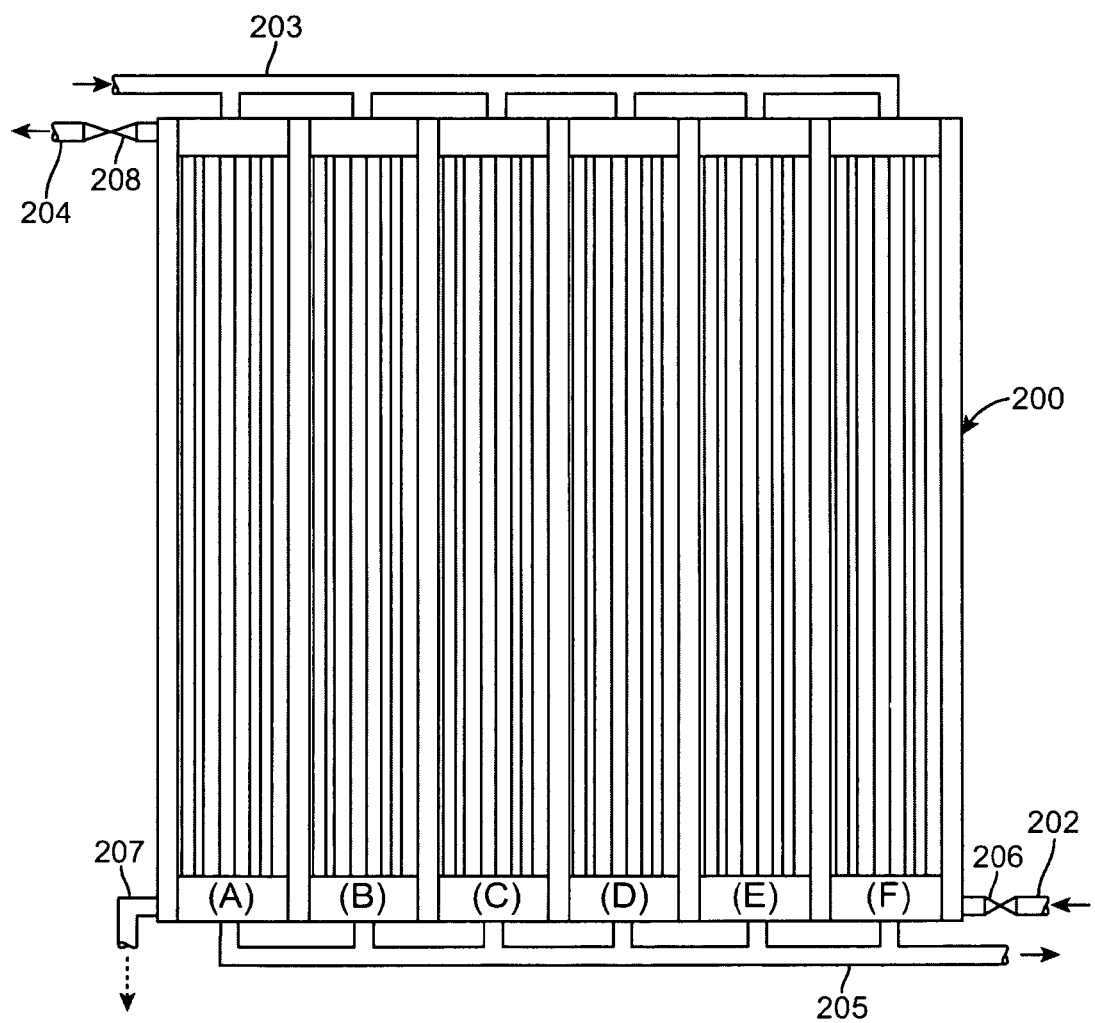
FIG. 7 schematically depicts a plurality of modules contained in a single vessel.

Whereas FIG. 6 shows each of modules A-F surrounded by its own individual pressure containment vessel, FIG. 7 shows an alternate arrangement where a single tank 200 circulates a process liquid from a liquid inlet manifold 203 to a liquid outlet manifold 205 across six modules A'-F' that have open sides so that tank 200 provides a common gas space for contact with all of the modules. At the same time a gas inlet 202 delivers process gas to while a gas outlet 204 collects process gas from modules A'-F'. The vessel also includes a liquid outlet 207. Thus, FIG. 7 depicts an assemblage of multiple modules that can undergo laving or purging by the operation of two valves 206 and 208.

The arrangement of FIG. 7 reduces the number of valves per module required to effect laving and purging. Valves 206 and 208 may constitute part of a larger system of valves of the type generally illustrated by FIG. 6. In this manner each valve or set of valves may regulate a plurality of modules. Although the FIG. 7 shows the liquid flow in parallel flow the arrangement can work equally well for series flow through the modules.

Groups of modules or individual modules may contain additional valves, regulating means, and sequencing devices to perform other module control and/or operational functions. For example in addition to laving the control system may periodically alter the sequencing of the feed gas delivery to modules and the number of modules receiving feed gas. Copending application U.S. Ser. No. 12/258,204 filed Apr. 21, 2008 describes such additional operation in detail and are hereby incorporated by reference herein.

EXAMPLE

The following example was conducted to demonstrate the practice of laving a membrane bioreactor. A MiniKros® membrane module Model M7-500S-900-01N from Spectrum Laboratories (Rancho Dominguez, Calif.) was used as a membrane bioreactor for the conversion of carbon monoxide and hydrogen into ethanol and acetate. This membrane module contained asymmetric polysulfone hollow fibers with 0.5 mm inner diameter, 0.66 mm outer diameter, and a pore size rated at 500 kDa nominal MWCO. The active membrane surface area of the module was 1.31 $m^2$, based on the fiber outer diameter. The bio-pores had effective diameters in the range of 3 to 30 μm. The membrane cartridge had a total shell volume of approximately 290 $cm^3$. The temperature of the membrane cartridge was maintained at 37° C.

The membrane module was connected to a 7.5-liter Bio-Flo® 310 Fermentor from New Brunswick Scientific (Edison, N.J.). The fermentor contained 3.0 liters of the fermentation medium, which was agitated at 100 rpm and maintained at 37° C. The fermentation pH was initially at 5.9 and, after incolulation, controlled at no lower than 5.2 using 2 N KOH. The fermentation medium had the compositions shown in Tables 1&2. The medium was pumped from the fermentor, flowed through the lumen side of the membrane module, and returned to the fermentor at a recirculation flow rate of 1700 ml/min. The fermentor was sparged with $N_2$ at 100 std ml/min initially to maintain anaerobic conditions and switched to syngas overlay as described below.

Initially, the membrane module was inoculated with 600 ml of an active culture of *Clostridium ragsdalei* ATCC No. BAA-622 by injecting the inoculum into the shell space. The inoculum was slightly pressurized to allow excess liquid volume to pass through the membrane into the lumen and the microbial cells to enter the void space of the membrane wall. Subsequently, a gas containing approximately 38% CO, 34% $H_2$, and 23% $CO_2$ was fed to the shell side of the membrane module at about 0.2 bars (gauge) to displace the remaining inoculum liquid. The gas continued to be fed at 200-400 std ml/min throughout the remainder of the fermentation run and the residual gas from the module was directed to the fermentor headspace and exited the fermentor through a condenser and a vent filter. The system was first operated in the batch mode for 46.5 hours to accumulate microbial cells within the porous membrane wall. Then, the system was switched to continuous operation, with continuous withdrawal of the fermentation liquid for product recovery and replenish of fresh medium at 60 ml/hr.

The gas pressure on the shell side was maintained at 0.2 bars in the first 74 hours, at 0.34 bars during the period of t=74 to 100 hours, and increased to 1.1 bars after 100 hours. The liquid pressure in the lumen was at 0.24 bars at the inlet and 0.03 bars at the outlet during the first 100 hours of the run and increased to 0.85 bars at the inlet and 0.68 bars at the outlet after t=100 hours. The gas uptake rates were about 0.4 mmol/min for $H_2$ and 0.8 mmol/min for CO at t=100 hours, gradually increased afterwards, and stabilized at 0.8 mmol/min for $H_2$ and 1.5 mmol/min for CO by t=135 hours.

The laving operation was started at t=143.4 hours. A solenoid valve was installed in the gas feed line and controlled by a programmable timer/controller. The timer/controller was programmed to have repeated cycles, each with 10 minutes of ON period (solenoid valve open) followed by 40 seconds of OFF period (solenoid valve closed). When the solenoid valve was closed, the gas pressure in the shell space of the membrane module decreased over time, due to consumption in the membrane module and escaping through the exhaust gas outlet, to about 0.8 bars at the end of the 40 seconds period. The fermentation with laving was continued till t=182 hr and the gas uptake rates remained stable at 0.8 mmol/min for $H_2$ and 1.5 mmol/min for CO.

The product concentrations in the withdrawn fermentation liquid were 1.6 g/L ethanol and 0.7 g/L acetate at t=93 hours and increased to 4.2 g/L ethanol and 4.0 g/L acetate at t=167 hours

The invention claimed is:

1. A process for converting a feed gas comprising a mixture of at least one of CO or a mixture of $CO_2$ and $H_2$ under anaerobic conditions using a bioreactor containing microorganisms to produce a liquid product wherein a liquid permeable membrane partitions the microorganisms from a liquid phase, retains the microorganisms in direct contact with the gas phase to produce the liquid product and delivers the liquid product to a liquid phase on the side of the substrate opposite the gas phase and the anaerobic conditions include the feed gas having an oxygen concentration of less than 1000 ppm and the liquid phase having a redox potential in the range of less than −200 mV, said process comprising:
   a) passing the feed gas to a gaseous phase for contact with a gas contacting side of a membrane that retains microorganisms in a plurality of bio-pores defined by a biolayer and having effective diameters of at least 1 μm over at least a portion of the pore length for retaining the microorganisms therein as the biolayer and a porous surface on the gas contacting side that presents open ends of the bio-pores to the feed gas;
   b) passing a liquid phase over a liquid contacting side of the substrate comprising a hydration layer that controls the flow of product containing liquid from bio-layer;
   c) maintaining sufficient positive pressure on the gas contacting side relative to the liquid contacting side to establish a first differential pressure such that there is a higher pressure on the gas contacting side than the liquid contacting side to transport the feed gas and the liquid products in co-directional flow from the gas contacting side to the liquid contacting side for a limited period of time; and,
   d) periodically subjecting the bio-layer to a laving cycle by reducing the first differential pressure such that liquid from the liquid contacting side laves into the biolayer, the laved liquid remains within the biopores during the laving cycle and the pressure on the liquid contacting side does not exceed the pressure on the gas contacting side.

2. The process of claim 1 wherein the substrate comprises an asymmetric hydrophilic membrane.

3. The process of claim 2 wherein the process includes a purge cycle wherein the pressure on the liquid side of the membrane exceeds the pressure on the gas side of the membrane by a sufficient amount such that liquid flows from the liquid contacting side and out of the biopores onto the gas contacting side to flush microorganisms and/or extra cellular material from the bio-pores.

4. The process of claim 2 wherein the asymmetric membrane comprises a hydration layer in the form of a semi-permeable skin on a porous polymer that provides the biolayer, the semi-permeable skin having a thickness of less than 10 μm and a porous polymer defines the gas contact side of the member, the porous polymer layer having a thickness of at least 50 μm and defining the gas contact side of the membrane.

5. The process of claim 4 wherein the semi-permeable skin is rated at a nominal MWCO of less than 300 kDa and the porous polymer defines bio-pores with effective diameters that do not exceed 100 μm.

6. The process of claim 2 wherein the asymmetric membrane is a composite membrane comprising a semi-permeable skin layer of one material as the hydration layer over a porous substrate of another material to provide the biopore layer.

7. The process of claim 2 wherein the bio-layer and hydration layer comprise the same material.

8. The process of claim 7 wherein the asymmetric membrane consists essentially of a semi-permeable skin and porous polymer both comprising polysulfone, polyethersulfone or polyvinyl chloride.

9. The process of claim 1 wherein the feed gas comprises synthesis gas.

10. The process of claim 9 wherein a liquid recovery conduit recovers an ethanol containing liquid as the product containing liquid.

11. The process of claim 1 wherein the microorganisms produce a liquid product comprising at least one of ethanol, n-butanol, hexanol, acetic acid, and butyric acid.

12. The process of claim 1 wherein the membrane comprises a plurality of hollow fiber membranes.

13. The process of claim 12 wherein the hollow fiber membranes extend vertically, the liquid product passes through the lumens of the asymmetric membrane and the feed gas passes across the outside of the asymmetric membrane.

14. The process of claim 1 wherein the microorganisms in the bio-layer comprise a mono-culture or a co-culture of at least one of Clostridium ragsdalei, Butyribacterium methylotrophicum, Clostridium Ljungdahlii and Clostridium carboxidivorans.

15. The process of claim 1 wherein the laving cycle occurs at a frequency of 10 seconds to 20 minutes and the duration of the laving cycle lasts from 0.5 seconds to 10 minutes.

16. A process for converting a feed gas comprising a mixture of at least one of CO or a mixture of $CO_2$ and $H_2$ under anaerobic conditions using a bioreactor containing microorganisms to produce a liquid product and delivering the liquid product to a product containing liquid wherein the feed gas has an oxygen concentration of less than 1000 ppm, said process comprising:
  a) passing the feed gas to a plurality of modules each containing an asymmetric hydrophilic membrane having a gas contacting side in contact with the feed gas, a bio-layer defining a plurality of bio-pores having effective diameters of at least 1 μm over at least a portion of the pore length for retaining microorganisms therein, and a porous surface on the bio-layer defining the gas contacting side that presents open ends of the bio-pores to the feed gas,
  b) passing a liquid phase to the plurality of modules and in each module contacting the liquid with a liquid contacting side of the asymmetric hydrophilic membrane comprising a hydration layer that provides a controlled flow of product containing liquid from the bio-layer into the liquid phase to supply the product containing liquid and maintaining the liquid phase with a redox potential in the range of less than −200 mV;
  c) maintaining sufficient positive pressure on the gas contacting side relative to the liquid contacting side to establish a first differential pressure such that there is a higher pressure on the gas contacting side than the liquid contacting side in at least a portion of the modules to transport the feed gas and the liquid products in co-directional flow from the gas contacting side to the liquid contacting side;
  d) periodically subjecting the bio-layer in a portion of the modules to a laving cycle in which liquid from the liquid contacting side laves into the biopores and the laved liquid remains within the biopores during the laving cycle by reducing the first pressure differential so that the pressure on the gas contacting side is approximately equal to the pressure on the liquid contacting side; and,
  e) sequentially changing the modules that are subjected to the laving cycle.

17. The process of claim 16 wherein each module sequentially undergoes a laving cycle at frequency of 2 to 15 minutes and for a duration of 1 minute to 10 minutes.

18. The process of claim 16 wherein at least one module is subjected to a laving cycle and at least one module undergoes a purge cycle wherein the pressure on the liquid side of the membrane exceeds the pressure on the gas side of the membrane by a sufficient amount such that liquid flows from the liquid contacting side and out of the biopores onto the gas contacting side to flush microorganisms and/or extra cellular material from the bio-pores.

19. The process of claim 16 wherein the feed gas contains at least one of CO or a mixture of $CO_2$ and $H_2$ and the microorganisms convert the feed gas under anaerobic conditions to a liquid product comprising at least one of ethanol, n-butanol, hexanol, acetic acid, and butyric acid.

20. The process of claim 16 wherein the asymmetric membrane comprises a hydration layer in the form of a semi-permeable skin on a porous polymer that provides the bio-layer, the semi-permeable skin having a thickness of less than 10 μm and a porous polymer defines the gas contact side of the member, the porous polymer layer having a thickness of at least 50 μm and defining the gas contact side of the membrane.

21. The process of claim 16 wherein the semi-permeable skin is rated at a nominal MWCO of less than 300 kDa and the porous polymer defines bio-pores with effective diameters that do not exceed 100 μm.

22. The process of claim 16 wherein the feed gas is synthesis gas, the bio-pores of the membrane retain a microorganism that produces ethanol and a liquid recovery conduit recovers an ethanol containing liquid as the product containing liquid.

23. The process of claim 16 wherein the asymmetric membrane comprises a plurality of hollow fiber membranes wherein the hollow fiber members extend vertically, the liquid product passes through the lumens of the asymmetric membrane and the feed gas passes across the outside of the asymmetric membrane.

24. The process of claim 16 wherein the microorganisms in the bio-pores comprise a mono-culture or a co-culture of at least one of Clostridium ragsdalei, Butyribacterium methylotrophicum, Clostridium Ljungdahlii and Clostridium carboxidivorans.

25. A process for converting a feed gas comprising a mixture of at least one of CO or a mixture of $CO_2$ and $H_2$ under anaerobic conditions using a bioreactor comprising a plurality of membrane modules containing microorganisms to produce a liquid product and delivering the liquid product to a product containing liquid wherein the feed gas has an oxygen concentration of less than 1000 ppm, said process comprising:
  a) passing the feed gas to a plurality of modules each containing an asymmetric hydrophilic hollow fiber membrane having an outer surface defining a gas contacting side in contact with the feed gas, a bio-layer defining a plurality of bio-pores having effective diameters of at least 1 μm over at least a portion of the pore length for retaining microorganisms in the biopores, and a porous surface on the bio-layer defining the gas contacting side that presents open ends of the bio-pores to the feed gas;
  b) passing a product containing liquid to the plurality of modules and in each module over a liquid contacting side defined by the lumen of the asymmetric hydrophilic membrane comprising a hydration layer that controls the flow of product containing liquid from bio-layer and defines the liquid contact side of the membrane;
  c) regularly maintaining the pressure on the gas contacting side of the modules higher than the pressure on the liquid contacting side of the modules to transport the feed gas and the liquid products in co-directional flow from the gas contacting side to the liquid contacting side;
  d) periodically laving the bio-layer in a portion of the modules with a laving cycle by decreasing the pressure of the gas contacting side relative to the liquid contacting side so that liquid from the liquid contacting side laves into the biopores and the laved liquid remains within the biopores during the laving cycle and the pressure on the gas contacting side remains at least equal to the pressure on the liquid contacting side;
  e) periodically purging the biolayer in at least one of the modules with a purge cycle wherein the pressure on the liquid side of the membrane exceeds the pressure on the gas side of the membrane by a sufficient amount such that liquid flows from the liquid contacting side and out of the biopores onto the gas contacting side to flush microorganisms and/or extra cellular material from the bio-pores; and, f) alternating the modules that are subjected to the laving cycle and the purge cycle so that all of the modules periodically undergo laving and purging.

26. The process of claim 25 wherein each module sequentially undergoes a laving cycle at frequency of 2 to 15 min. and for a duration of 10 seconds to 10 minutes and each module sequentially undergoes a purge cycle at frequency of 24 to 1000 hours and for a duration of 10 seconds to 10 minutes.

\* \* \* \* \*

UNITED STATES PATENT AND TRADEMARK OFFICE
CERTIFICATE OF CORRECTION

PATENT NO.       : 8,211,692 B2
APPLICATION NO.  : 12/258193
DATED            : July 3, 2012
INVENTOR(S)      : Rathin Datta et al.

It is certified that error appears in the above-identified patent and that said Letters Patent is hereby corrected as shown below:

On the Title page, Item (54) and Col. 1, Lines 1-3 delete:

Title: "BIOCONVERSION PROCESS USING LIQUID PHASE HAVING TO ENHANCE GAS PHASE CONVERSION"

and insert:

--BIOCONVERSION PROCESS USING LIQUID PHASE LAVING TO ENHANCE GAS PHASE CONVERSION.--

Signed and Sealed this
Twenty-fifth Day of September, 2012

David J. Kappos
*Director of the United States Patent and Trademark Office*